(12) United States Patent
Hashimoto et al.

(10) Patent No.: US 10,028,663 B2
(45) Date of Patent: Jul. 24, 2018

(54) PHOTOACOUSTIC MEASUREMENT APPARATUS AND PROBE

(71) Applicant: FUJIFILM Corporation, Tokyo (JP)

(72) Inventors: Atsushi Hashimoto, Ashigarakami-gun (JP); Kaku Irisawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/689,390

(22) Filed: Aug. 29, 2017

(65) Prior Publication Data

US 2017/0360304 A1 Dec. 21, 2017

Related U.S. Application Data (63) Continuation of application No. PCT/JP2016/052414, filed on Jan. 28, 2016.

(30) Foreign Application Priority Data

Mar. 13, 2015 (JP) .................................. 2015-050403

(51) Int. Cl.
G01N 21/00 (2006.01)
A61B 5/00 (2006.01)
(Continued)

(52) U.S. Cl.
CPC .......... *A61B 5/0095* (2013.01); *A61B 5/0035* (2013.01); *A61B 8/0891* (2013.01);
(Continued)

(58) Field of Classification Search
CPC ............. G01N 21/1702; G01N 21/171; G01N 21/1717; G01N 21/255; G01N 29/2418
(Continued)

(56) References Cited

U.S. PATENT DOCUMENTS

| 7,924,423 B2 * | 4/2011 | Van Neste ......... G01N 21/1702 356/300 |
| 2009/0153873 A1 * | 6/2009 | Chan .................. G01N 21/4795 356/495 |

(Continued)

FOREIGN PATENT DOCUMENTS

| JP | 2013-55988 A | 3/2013 |
| JP | 2014-128321 A | 7/2014 |

(Continued)

OTHER PUBLICATIONS

International Preliminary Report on Patentability and Written Opinion of the International Searching Authority (Forms PCT/IB/326, PCT/IB/373 and PCT/ISA/237) issued in International Application No. PCT/JP2016/052414 dated Sep. 28, 2017, together with an English translation.

(Continued)

*Primary Examiner* — Tarifur Chowdhury
*Assistant Examiner* — Md M Rahman
(74) *Attorney, Agent, or Firm* — Birch, Stewart, Kolasch & Birch, LLP (57) ABSTRACT

In a photoacoustic measurement apparatus and a probe, artifacts due to photoacoustic waves generated in a surface portion of a subject are reduced without increasing the repetition period of photoacoustic measurement. A measurement light emitting unit emits measurement light toward a subject. An acoustic wave detector detects photoacoustic waves generated within the subject due to the measurement light. A correction light source emits correction light toward the subject. A light intensity detector detects reflected light generated by reflection of the correction light, which is emitted toward the subject, from the subject. In a probe, the correction light source and the light intensity detector are (Continued)

disposed between the measurement light emitting unit and the acoustic wave detector.

28 Claims, 5 Drawing Sheets

(51) Int. Cl.
  *A61B 8/00* (2006.01)
  *G01N 29/24* (2006.01)
  *A61B 8/14* (2006.01)
  *A61B 8/08* (2006.01)

(52) U.S. Cl.
  CPC ............ *A61B 8/145* (2013.01); *A61B 8/4416* (2013.01); *A61B 8/4444* (2013.01); *G01N 29/2406* (2013.01); *A61B 2562/0242* (2013.01)

(58) Field of Classification Search
  USPC .......................................................... 356/432
  See application file for complete search history.

(56) References Cited

U.S. PATENT DOCUMENTS

| | | |
|---|---|---|
| 2011/0306857 A1 | 12/2011 | Razansky et al. |
| 2013/0160557 A1 | 6/2013 | Nakajima et al. |
| 2014/0187924 A1 | 7/2014 | Oishi |
| 2014/0378811 A1 | 12/2014 | Nanaumi |

FOREIGN PATENT DOCUMENTS

| | | |
|---|---|---|
| JP | 2015-24125 A | 2/2015 |
| WO | WO 2011/052061 A1 | 5/2011 |
| WO | WO 2013/031586 A1 | 3/2013 |
| WO | WO 2013/185784 A1 | 12/2013 |

OTHER PUBLICATIONS

International Search Report (Form PCT/ISA/210) issued in International Application No. PCT/JP2016/052414 dated Mar. 8, 2016, together with an English translation.

Extended European Search Report, dated Mar. 12, 2018, for corresponding European Application No. 10764537.3.

\* cited by examiner

PHOTOACOUSTIC MEASUREMENT APPARATUS AND PROBE

CROSS-REFERENCE TO RELATED APPLICATIONS

This application is a Continuation of PCT International Application No. PCT/JP2016/052414 filed on Jan. 28, 2016, which claims priority under 35 U.S.C § 119(a) to Japanese Patent Application No. 2015-050403 filed on Mar. 13, 2015. Each of the above application(s) is hereby expressly incorporated by reference, in its entirety, into the present application.

BACKGROUND OF THE INVENTION

1. Field of the Invention

The present invention relates to a photoacoustic measurement apparatus, more specifically, to a photoacoustic measurement apparatus for detecting photoacoustic waves generated in a subject after emitting light to the subject. In addition, the present invention relates to a probe used in such a photoacoustic measurement apparatus.

2. Description of the Related Art

As a kind of image examination method capable of examining the state of the inside of a living body in a non-invasive manner, an ultrasound examination method is known. In ultrasound examination, an ultrasound probe capable of transmitting and receiving ultrasound waves is used. In a case where ultrasound waves are transmitted from the ultrasound probe to the living body (subject), the ultrasound waves propagate through the living body to be reflected on the tissue interface. By receiving the reflected sound waves using the ultrasound probe and calculating the distance based on the time until the reflected ultrasound waves return to the ultrasound probe, it is possible to image the state of the inside.

In addition, photoacoustic imaging for imaging the inside of the living body using the photoacoustic effect is known. Generally, in photoacoustic imaging, pulsed laser light is emitted into the living body that is a subject. In the living body, a living tissue absorbs the energy of the pulsed laser light, and ultrasound waves (photoacoustic waves) are generated due to adiabatic expansion due to the energy. By detecting the photoacoustic waves using an ultrasound probe or the like and forming a photoacoustic image based on the detection signal, it is possible to visualize the inside of the living body based on the photoacoustic signal.

In the photoacoustic measurement, measurement is performed mainly in a state in which a probe is pressed against the surface of the subject. In a case where measurement light is emitted from the probe, strong photoacoustic waves are often generated in a surface portion of the subject on which the measurement light is incident. The main source of the photoacoustic waves is melanin of the skin surface. Photoacoustic waves generated in the surface portion of the subject travel near the surface or are multi-reflected, and accordingly the photoacoustic waves are detected by the probe together with a photoacoustic wave signal generated in a region of interest inside the subject. This is the cause of the occurrence of artifacts (virtual image).

In order to solve the aforementioned problem, in JP2013-55988A, first light and second light having different wavelengths are emitted to the subject, and a photoacoustic wave is detected for each of the first light and the second light. The wavelength of the first light and the wavelength of the second light are selected such that the ratio between the strength of a detection signal corresponding to a light absorber inside the subject due to the emission of the first light and the strength of a detection signal corresponding to the surface portion of the subject is smaller than the ratio between the strength of a detection signal corresponding to a light absorber inside the subject due to the emission of the second light and the strength of a detection signal corresponding to the surface portion of the subject. By reducing unnecessary signals generated in the surface portion of the subject by calculating the difference between a photoacoustic image obtained by the emission of the first light and a photoacoustic image obtained by the emission of the second light, it is possible to obtain an image with few artifacts.

SUMMARY OF THE INVENTION

In JP2013-55988A, however, in order to reduce artifacts, it is necessary to emit measurement light beams having two wavelengths and detect photoacoustic waves twice. That is, in order to obtain one photoacoustic image, it is necessary to emit two measurement light beams. Accordingly, there is a problem that the repetition period in the case of repeatedly generating a photoacoustic image is longer than that in a case where one photoacoustic image is obtained by emission of one measurement light. Usually, for measurement light used for photoacoustic measurement, high energy is required. Accordingly, since light sources for two wavelengths should be prepared as light sources for emitting such measurement light, there is also a problem that the cost increases.

In view of the above circumstances, it is an object of the present invention to provide a photoacoustic measurement apparatus capable of reducing artifacts due to photoacoustic waves generated in the surface portion of the subject even in a case where single measurement light is used. In addition, the present invention provides a probe used in such a photoacoustic measurement apparatus.

In order to achieve the aforementioned object, the present invention provides a probe comprising: a measurement light emitting unit that emits measurement light toward a subject; an acoustic wave detector that detects a photoacoustic wave generated within the subject due to the measurement light; a correction light source that emits correction light toward the subject; and a light intensity detector that detects reflected light generated by reflection of the correction light, which is emitted toward the subject, from the subject. The correction light source and the light intensity detector are disposed between the measurement light emitting unit and the acoustic wave detector.

In the present invention, it is preferable that the measurement light emitting unit includes a light emission surface, which is a surface from which the measurement light is emitted, and the acoustic wave detector includes an acoustic wave detection surface, which is a surface on which the acoustic wave is incident, and that the correction light source and the light intensity detector are disposed within the same plane as the light emission surface and the acoustic wave detection surface.

The acoustic wave detector may include a plurality of detector elements arranged along one direction.

In the probe of the present invention, a plurality of the measurement light emitting units may be provided, and the plurality of measurement light emitting units may face each other with the acoustic wave detector interposed therebetween in a direction perpendicular to the arrangement direction of the detector elements. In this case, it is preferable that the correction light source and the light intensity detector are disposed between the measurement light emitting unit and the acoustic wave detector.

The correction light source may be configured to include a first correction light source, which is arranged along the arrangement direction of the detector elements and emits first correction light having a first wavelength, and a second correction light source, which is arranged along the arrangement direction of the detector elements and emits second correction light having a second wavelength different from the first wavelength.

In the above, the correction light source may include a plurality of the first correction light sources and a plurality of the second correction light sources. The plurality of first correction light sources and the plurality of second correction light sources may be alternately arranged along the arrangement direction of the detector elements.

The light intensity detector may be configured to include a first light intensity detector, which is arranged along the arrangement direction of the detector elements and selectively detects correction light having the first wavelength, and a second light intensity detector, which is arranged along the arrangement direction of the detector elements and selectively detects correction light having the second wavelength.

The first light intensity detector may include a first optical filter that transmits light having the first wavelength and does not transmit light having the second wavelength. The second light intensity detector may include a second optical filter that transmits light having the second wavelength and does not transmit light having the first wavelength.

The light intensity detector may include a plurality of the first light intensity detectors and a plurality of the second light intensity detectors. The plurality of first light intensity detectors and the plurality of second light intensity detectors may be alternately arranged along the arrangement direction of the detector elements.

A wavelength of the measurement light and a wavelength of the correction light may be different from each other. In this case, the light intensity detector may further detect reflected light generated by reflection of the measurement light, which is emitted toward the subject, from the subject.

The correction light source may be configured to include a light emitting diode.

In addition, the present invention provides a photoacoustic measurement apparatus comprising: the above-described probe of the present invention; a light source that emits the measurement light; a signal processing device that has a signal processing unit that performs signal processing based on a detection signal of the photoacoustic wave detected by the acoustic wave detector, a melanin amount estimation unit that estimates an amount of melanin based on a detection signal of the reflected light detected by the light intensity detector, and a correction unit that corrects signal processing of the signal processing unit.

In the photoacoustic measurement apparatus of the present invention, it is preferable that the signal processing unit generates a photoacoustic image based on the detection signal of the photoacoustic wave.

In a case where the probe is configured to include a first correction light source and a second correction light source, the melanin amount estimation unit may estimate the amount of melanin based on a detection signal of reflected light of the first correction light detected by the light intensity detector and a detection signal of reflected light of the second correction light detected by the light intensity detector.

Alternatively, in a case where the probe is configured to further detect reflected light of the measurement light, the melanin amount estimation unit may estimate the amount of melanin based on a detection signal of reflected light of the correction light detected by the light intensity detector and a detection signal of reflected light of the measurement light detected by the light intensity detector.

The photoacoustic measurement apparatus and the probe of the present invention can measure photoacoustic waves even with single measurement light and can reduce artifacts due to photoacoustic waves generated in the surface portion of the subject.

DESCRIPTION OF THE PREFERRED EMBODIMENTS

Figure 1:
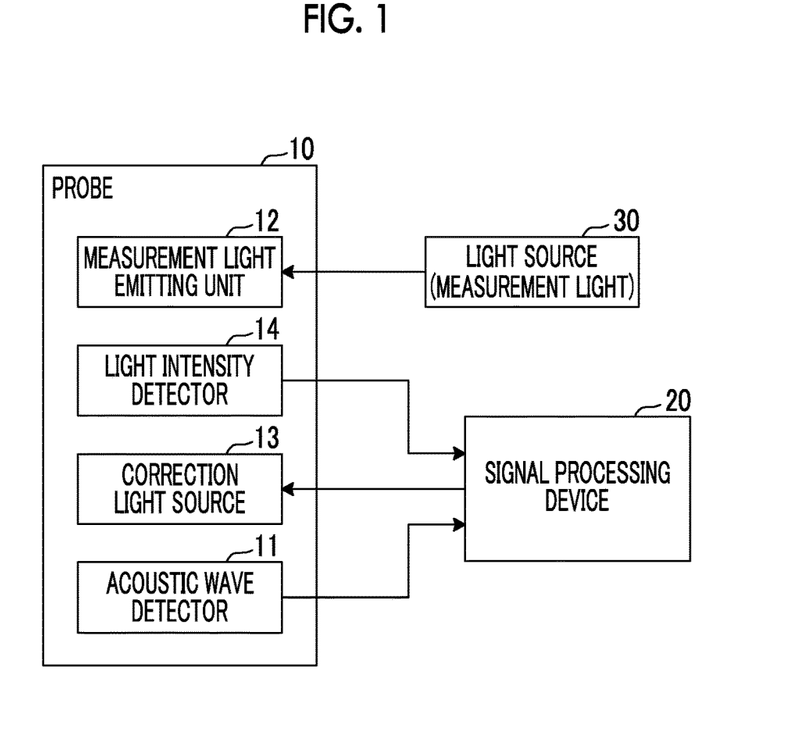
FIG. 1 is a block diagram schematically showing a photoacoustic measurement apparatus including a probe according to a first embodiment of the present invention.

Hereinafter, embodiments of the present invention will be described in detail with reference to the diagrams. FIG. 1 shows the schematic configuration of a photoacoustic measurement apparatus including a probe according to a first embodiment of the present invention. The photoacoustic measurement apparatus includes a probe 10, an ultrasound unit (signal processing device) 20, and a light source 30.

The light source 30 emits measurement light. The measurement light emitted from the light source 30 is guided to the probe 10, for example, using light guide means, such as an optical fiber. The light source 30 is, for example, a solid state laser light source using an yttrium aluminum garnet (YAG), alexandrite, or the like. The wavelength of the measurement light is appropriately selected according to a measurement target. For example, a wavelength at which absorption in blood is stronger than that in the surrounding tissue, such as muscle fat, is selected. Hereinafter, an example in which light having a wavelength of 755 nm is mainly used as measurement light will be described. The type of the light source is not particularly limited, and the light source 30 may be a laser diode light source (semiconductor laser light source), or may be a light amplification type laser light source using a laser diode light source as a seed light source. Light sources other than the laser light source may be used.

The probe 10 has an acoustic wave detector 11, a measurement light emitting unit 12, a correction light source 13, and a light intensity detector 14. The measurement light emitting unit 12 emits measurement light, which is emitted from the light source 30, toward the subject. The acoustic wave detector 11 is an electroacoustic conversion unit that detects an acoustic wave and converts the detected acoustic wave into an electrical signal. The acoustic wave detector 11 detects photoacoustic waves generated within the subject due to the measurement light. The acoustic wave detector 11 includes, for example, a plurality of detector elements arranged along one direction. The detection signal of the acoustic wave detected by the acoustic wave detector 11 is transmitted to the signal processing device 20. The signal processing device 20 is a device that performs signal processing, and is typically a device having a processor, a memory, a bus, and the like.

The correction light source 13 emits correction light toward the subject. The correction light source 13 includes, for example, a light emitting diode. The energy of the correction light emitted from the correction light source 13 may be lower than the energy of the measurement light emitted from the light source 30. The lighting of the correction light source 13 is controlled by the signal processing device 20, for example.

The light intensity detector 14 detects reflected light generated by the reflection of the correction light, which is emitted from the correction light source 13 toward the subject, from the subject. The light intensity detector 14 includes, for example, a photodiode. The detection signal of the reflected light detected by the light intensity detector 14 is transmitted to the signal processing device 20. The configuration of the light intensity detector 14 is not particularly limited as long as it is possible to output an electrical signal corresponding to incidence light.

The correction light source 13 and the light intensity detector 14 are disposed between the acoustic wave detector 11 and the measurement light emitting unit 12. The probe 10 may have a plurality of correction light sources 13 and a plurality of light intensity detectors 14. The plurality of correction light sources 13 and the plurality of light intensity detectors 14 may be arranged along the arrangement direction of detector elements in the acoustic wave detector 11.

The probe 10 may have a plurality of measurement light emitting units 12. The probe 10 has, for example, two measurement light emitting units 12. The plurality of measurement light emitting units 12 may be disposed so as to face each other with the acoustic wave detector 11 interposed therebetween in a direction perpendicular to the arrangement direction of the detector elements in the acoustic wave detector 11. In that case, the correction light source 13 and the light intensity detector 14 may be disposed between the acoustic wave detector 11 and the measurement light emitting unit 12.

Figure 2:
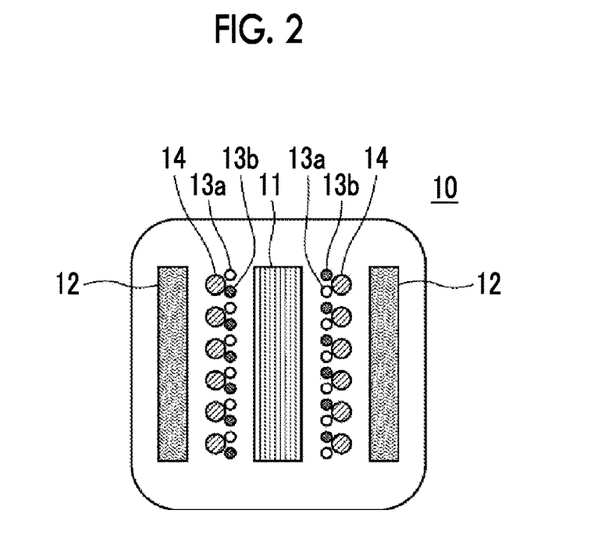
FIG. 2 is a plan view showing a probe.

FIG. 2 is a plan view of the probe 10 when viewed from the side in contact with a subject. The type of the probe 10 is not particularly limited, and a linear probe may be used, or a convex probe or a sector probe may be used. The acoustic wave detector 11 is disposed in a central portion of a housing (cover) forming the probe body. The longitudinal direction of the acoustic wave detector 11 matches the arrangement direction of the detector elements. In FIG. 2, the two measurement light emitting units 12 are disposed so as to face each other with the acoustic wave detector 11 interposed therebetween in a direction perpendicular to the longitudinal direction of the acoustic wave detector 11. In addition, the probe 10 has a plurality of light intensity detectors 14. The plurality of light intensity detectors 14 are arranged in a row along the longitudinal direction of the acoustic wave detector 11.

It is preferable that the correction light source 13 includes a plurality of light sources that emit correction light beams having a plurality of different wavelengths. In FIG. 2, the correction light source 13 includes a first correction light source 13a that emits first correction light having a first wavelength and a second correction light source 13b that emits second correction light having a second wavelength. The first correction light source 13a emits, for example, light having a wavelength of 660 nm (first correction light) that is red light, and the second correction light source 13b emits, for example, light having a wavelength of 880 nm (second correction light) that is near infrared light.

The first correction light source 13a and the second correction light source 13b are arranged along the longitudinal direction of the acoustic wave detector 11. In FIG. 2, the correction light source 13 has a plurality of first correction light sources 13a and a plurality of second correction light sources 13b. The plurality of first correction light sources 13a and the plurality of second correction light sources 13b are alternately arranged along the longitudinal direction of the acoustic wave detector 11. The position of the correction light source 13 and the position of the light intensity detector 14 may be reversed.

The correction light source 13 and the light intensity detector 14 are disposed within the same plane as an acoustic wave incidence surface, which is a surface of the acoustic wave detector 11 on which an acoustic wave is incident, and a light emission surface, which is a surface of the measurement light emitting unit 12 from which measurement light is emitted. "Being disposed within the same plane" means that the correction light source 13, the light intensity detector 14, the acoustic wave incidence surface, and the light emission surface are present on a surface that is brought into contact with the subject when pressed against the subject. The side of the probe 10 in contact with the subject may be curved or inclined, or may have a slit, or may have a step difference. Also in such a case, it is assumed that the correction light source 13 and the light intensity detector 14 are present within the same plane as the acoustic wave detection surface and the light emission surface. The arrangement of the respective elements shown in FIG. 2 is an example, and the number of elements, the shape of each element, and the positional relationship between elements are not limited thereto.

Figure 3:
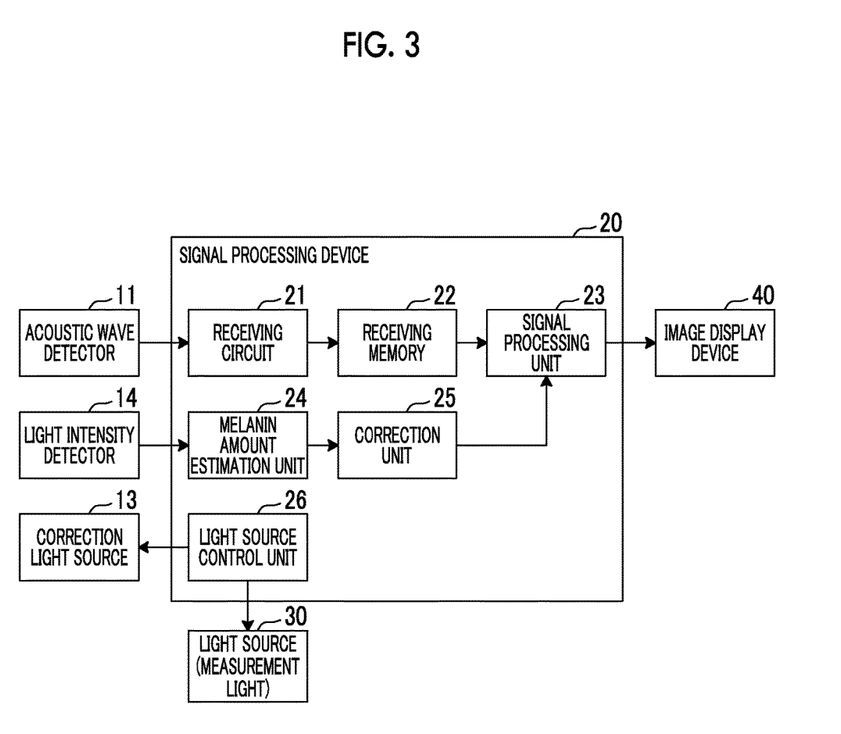
FIG. 3 is a block diagram showing a signal processing device.

FIG. 3 shows the signal processing device 20. The signal processing device 20 has a receiving circuit 21, a receiving memory 22, a signal processing unit 23, a melanin amount estimation unit 24, a correction unit 25, and a light source control unit 26.

The receiving circuit 21 receives a detection signal output from the acoustic wave detector 11 of the probe 10, and stores the received detection signal in the receiving memory 22. Typically, the receiving circuit 21 includes a low noise amplifier, a variable gain amplifier, a low pass filter, and an analog to digital converter (AD converter). The detection signal of the acoustic wave detector 11 is amplified by the low noise amplifier, and then gain adjustment according to the depth is performed by the variable gain amplifier and a high-frequency component is cut by the low pass filter. Then, conversion into a digital signal is performed by the AD converter, and the digital signal is stored in the receiving memory 22. The receiving circuit 21 is formed by one integrated circuit (IC), for example. As the receiving memory 22, for example, a semiconductor memory is used.

The acoustic wave detector 11 outputs a detection signal of the photoacoustic wave, and the detection signal (sampling data) of the photoacoustic wave after AD conversion is stored in the receiving memory 22. The signal processing unit 23 reads the detection signal of the photoacoustic wave from the receiving memory 22, and performs signal processing on the read detection signal of the photoacoustic wave. The signal processing unit 23 generates a photoacoustic image based on the detection signal of the photoacoustic wave, for example. The generation of a photoacoustic image includes, for example, image reconstruction such as phase matching addition, detection, and logarithmic conversion. The generated photoacoustic image is displayed on an image display device 40. The signal processing unit 23 is formed by large scale integration (LSI), such as a digital signal processor (DSP). The function of the signal processing unit 23 may be realized by software processing using a processor included in the signal processing device 20.

The melanin amount estimation unit 24 estimates the amount of melanin of the surface of the subject based on the detection signal of the reflected light with respect to the correction light output from the light intensity detector 14. It is known that melanin exhibits a spectrum in which the light absorption characteristic in the visible to near infrared region monotonously decreases with an increasing wavelength and that the spectral intensity in the entire wavelength region increases as the amount of melanin increases. The amount of melanin can be estimated based on the intensity of reflected light of light beams having a plurality of wavelengths. In order to estimate the amount of melanin using reflected light beams having a plurality of wavelengths, it is possible to use a known method.

The melanin amount estimation unit 24 estimates the amount of melanin based on the detection signal of the reflected light in a case where the first correction light source 13*a* (refer to FIG. 2) is lit and the detection signal of the reflected light in a case where the second correction light source 13*b* is lit. As in the example shown in FIG. 2, in a case where a plurality of light intensity detectors 14 are arranged along the longitudinal direction of the acoustic wave detector 11, the amount of melanin may be estimated at each position in the longitudinal direction. The melanin amount estimation unit 24 may estimate a degree indicating whether the amount of melanin of the surface of the subject is large or small, and it is not necessary to accurately quantify the amount of melanin. Emission of correction light and detection of reflected light may be performed multiple times, and the amount of melanin may be estimated using an average value, a median value, or the like of the detection signals of the plurality of reflected light beams.

The correction unit 25 corrects the signal processing of the signal processing unit 23 based on the amount of melanin estimated by the melanin amount estimation unit 24. The correction is performed, for example, by changing the brightness of the surface portion of the subject in the photoacoustic image generated by the signal processing unit 23 according to the estimated amount of melanin. For example, the correction unit 25 corrects the photoacoustic image by lowering the brightness of the surface portion of the subject as the estimated amount of melanin increases. In this case, since the brightness of the surface portion is lowered, it becomes easy to observe the inside of the subject.

The correction unit 25 may correct the photoacoustic image by changing the brightness of the entire photoacoustic image according to the estimated amount of melanin. More specifically, the gain of the photoacoustic image may increase as the estimated amount of melanin increases. In that case, since the brightness of the surface portion is saturated while the inner portion is drawn brightly, it becomes easy to observe the inside of the subject.

The correction unit 25 may change the brightness according to the estimated amount of melanin and the position or depth of the photoacoustic image. More specifically, the brightness of the deep portion of the image may be lowered as the estimated amount of melanin increases. If the amount of melanin is large, photoacoustic waves generated in the surface portion of the subject become strong. The photoacoustic waves cause multiple reflections to increase artifacts. By lowering the brightness of the deep portion, it is possible to obtain an image in which the influence of artifacts is reduced. Instead of the above, the brightness of the surface portion may be lowered, and the brightness of the deep portion of the image may be increased. In that case, it is possible to obtain an image easy to see (image easy to observe) by making the brightness of the entire image uniform.

Each of the melanin amount estimation unit 24 and the correction unit 25 may be formed by large scale integration (LSI), such as a digital signal processor (DSP), for example. Alternatively, these functions may be realized by software processing using a processor included in the signal processing device 20. The correcting unit 25 may be a part of the signal processing unit 23.

Estimation of the amount of melanin by the melanin amount estimation unit 24 is performed before the signal processing unit 23 performs signal processing or after the signal processing is performed. In a case where the estimation of the amount of melanin is performed before the signal processing, the signal processing unit 23 may perform signal processing according to the content of the correction of the correction unit 25. In a case where the estimation of the amount of melanin is performed after the signal processing, the correction unit 25 may correct the result of the signal processing of the signal processing unit 23.

The light source control unit 26 controls the light source 30 and the correction light source 13. For example, in the case of acquiring a photoacoustic image, the light source control unit 26 transmits an optical trigger signal to the light source 30 so that measurement light is emitted from the light source 30. The light source control unit 26 may control the photoacoustic wave sampling start timing or the like by transmitting a sampling trigger signal to the receiving circuit 21 in response to the emission of the measurement light. The area where photoacoustic waves are to be detected may be divided into a plurality of areas. In that case, emission of light to the subject and detection of photoacoustic waves may be performed for each area.

In the case of estimating the amount of melanin, the light source control unit 26 causes correction light to be emitted from the correction light source 13. In a case where the correction light source 13 has light sources that emit correction light beams having a plurality of wavelengths, the light source control unit 26 causes the correction light beams to be selectively emitted from these. For example, in a case where the correction light source 13 has a first correction light source 13*a* and a second correction light source 13*b* as shown in FIG. 2, the correction light beams are selectively emitted from these. The light source control unit 26 is formed by a programmable logic device (PLD), such as a field-programmable gate array (FPGA), for example.

Figure 4:
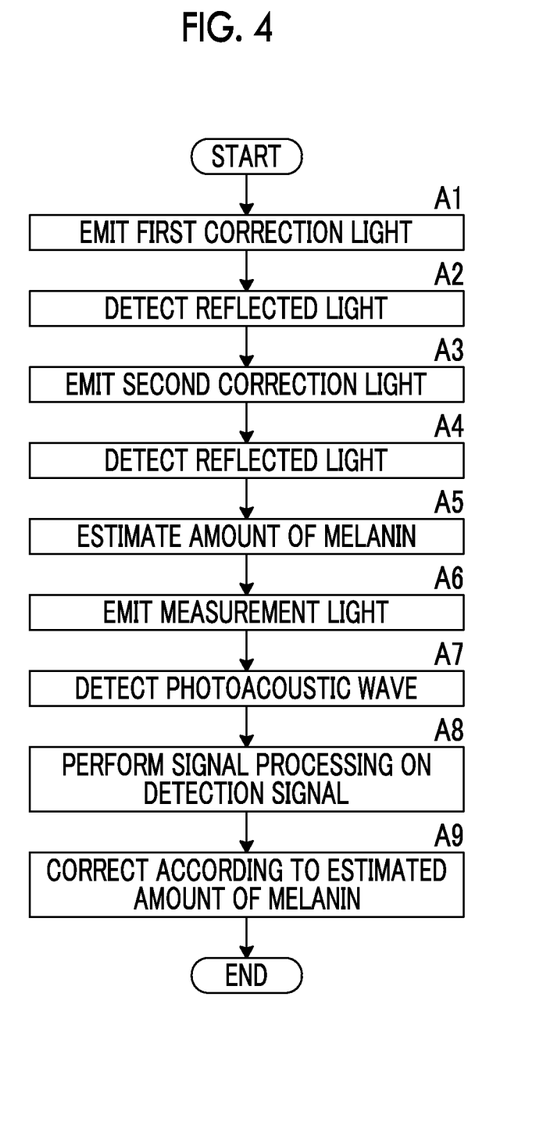
FIG. 4 is a flowchart showing the operation procedure of photoacoustic measurement.

Hereinafter, the operation procedure will be described. FIG. 4 shows a procedure of photoacoustic measurement. A doctor or the like presses the probe 10 against an examination part of the subject. The light source control unit 26 turns on the first correction light source 13*a* to emit the first correction light to the subject (step A1). The light intensity detector 14 detects reflected light of the first correction light, and transmits the detection signal to the signal processing device 20 (step A2).

Then, the light source control unit 26 turns on the second correction light source 13b to emit the second correction light to the subject (step A3). The light intensity detector 14 detects the reflected light of the second correction light, and transmits the detection signal to the signal processing device 20 (step A4). Either the emission of the first correction light or the emission of the second correction light may be performed first. The melanin amount estimation unit 24 estimates the amount of melanin of a portion, against which the probe 10 is pressed, based on the detection signal of the reflected light of the first correction light and the detection signal of the reflected light of the second correction light that have been received from the light intensity detector 14 (step A5).

Then, the light source control unit 26 causes the light source 30 to emit measurement light (step A6). The acoustic wave detector 11 detects photoacoustic waves generated within the subject due to the emission of the measurement light (step A7). The detection signal of the photoacoustic wave is input to the signal processing unit 23 through the receiving circuit 21 and the receiving memory 22. The signal processing unit 23 performs signal processing on the detection signal of the photoacoustic wave (step A8). The signal processing unit 23 generates a photoacoustic image, for example. The correction unit 25 corrects the signal processing of the signal processing unit 23, for example, image generation processing, according to the amount of melanin estimated in step A5 (step A9).

In the present embodiment, the correction light source 13 and the light intensity detector 14 are provided in the probe. The reflected light of the correction light emitted from the correction light source 13 is detected by the light intensity detector 14, the amount of melanin is estimated based on the detection signal of the reflected light, and signal processing on the detection signal of the photoacoustic wave is corrected. The photoacoustic wave generated in the surface portion of the subject is generated mainly due to melanin present in the surface portion of the subject. By correcting the signal processing on the photoacoustic wave according to the estimated amount of melanin, it is possible to reduce artifacts due to the photoacoustic wave generated in the surface portion of the subject. In the present embodiment, unlike in JP2013-55988A, it is not necessary to emit a plurality of measurement light beams in one photoacoustic measurement. Therefore, it is possible to reduce artifacts due to the photoacoustic wave generated in the surface portion of the subject without extending the repetition period in the case of repeatedly performing photoacoustic measurement.

In the present embodiment, the correction light source 13 and the light intensity detector 14 are disposed between the acoustic wave detector 11 and the measurement light emitting unit 12. By adopting such an arrangement, it is possible to estimate the amount of melanin in the vicinity of the acoustic wave detector 11 and the measurement light emitting unit 12. In addition, by arranging a plurality of correction light sources 13 (the first correction light source 13a and the second correction light source 13b) and the light intensity detectors 14 along the longitudinal direction of the acoustic wave detector 11 as shown in FIG. 2, data of the estimated amount of melanin can be obtained as one-dimensional distribution data. In this case, correction according to the position within the plane becomes possible.

In the case of a configuration in which the measurement light emitting unit 12 is provided in the probe 10, photoacoustic waves may be generated by absorption of a part of measurement light by the housing that forms the probe body in the vicinity of the measurement light emitting unit 12. The photoacoustic wave is transmitted through the surface portion of the housing and is detected by the acoustic wave detector 11, which may cause artifacts. In the present embodiment, since the correction light source 13 and the light intensity detector 14 are present between the acoustic wave detector 11 and the measurement light emitting unit 12, an interface having different acoustic impedance is formed between the acoustic wave detector 11 and the measurement light emitting unit 12. Therefore, it can be expected that photoacoustic waves generated in the vicinity of the measurement light emitting unit 12 are reflected and scattered at the interface. As a result, since it is difficult for the photoacoustic waves generated in the vicinity of the measurement light emitting unit 12 to be incident on the acoustic wave detector 11, it is possible to reduce artifacts caused by the photoacoustic waves.

Figure 5:
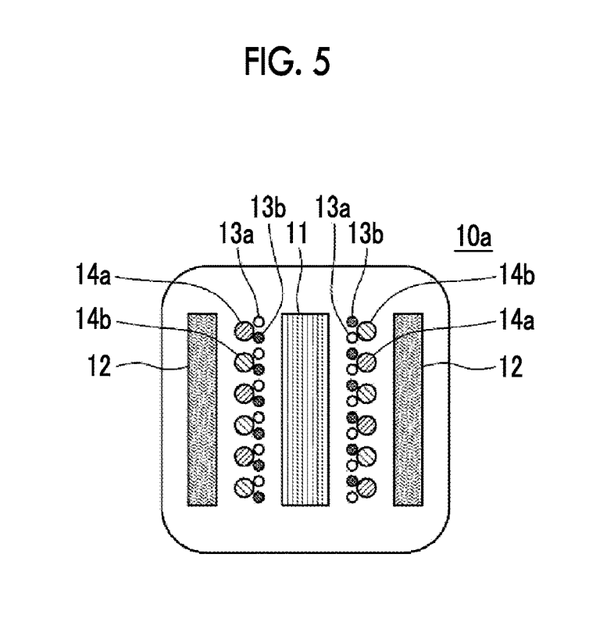
FIG. 5 is a plan view showing a probe according to a second embodiment of the present invention.

Subsequently, a second embodiment of the present invention will be described. FIG. 5 shows a probe according to the second embodiment of the present invention. The present embodiment is different from the first embodiment in that the light intensity detector 14 disposed in a probe 10a includes a plurality of light intensity detectors that selectively detect correction light beams having a plurality of wavelengths. Others may be the same as in the first embodiment.

The light intensity detector 14 includes a first light intensity detector 14a that selectively detects reflected light of the first correction light and a second light intensity detector 14b that selectively detects reflected light of the second correction light. The first light intensity detector 14a and the second light intensity detector 14b are arranged along the longitudinal direction of the acoustic wave detector 11. In FIG. 5, the light intensity detector 14 has a plurality of first light intensity detectors 14a and a plurality of second light intensity detectors 14b. The plurality of first light intensity detectors 14a and the plurality of second light intensity detectors 14b are alternately arranged along the longitudinal direction of the acoustic wave detector 11.

The first light intensity detector 14a includes an optical filter that transmits light having a first wavelength and does not transmit light having a second wavelength, for example. That is, the first light intensity detector 14a includes a first optical filter that transmits the first correction light and does not transmit the second correction light. The second light intensity detector 14b includes an optical filter that transmits the light having the second wavelength and does not transmit the light having the first wavelength, for example. That is, the second light intensity detector 14b includes an optical filter that transmits the second correction light and does not transmit the first correction light. By using such an optical filter, it is possible to selectively detect the first correction light or the second correction light.

For example, in a case where the wavelength of the first correction light is 660 nm and the wavelength of the second correction light is 880 nm, the first light intensity detector 14a includes an optical filter that transmits light having a wavelength of 660 nm and does not transmit light having a wavelength of 880 nm. As such an optical filter, a band pass filter in which a wavelength of 660 nm is included in the transmission band and 880 nm is not included in the transmission band, a short pass filter that transmits only light having a wavelength equal to or less than a wavelength shorter than the wavelength of 880 nm and longer than the wavelength of 660 nm, or the like can be considered. The second light intensity detector 14b includes an optical filter that transmits light having a wavelength of 880 nm and does not transmit light having a wavelength of 660 nm. As such an optical filter, a band pass filter in which a wavelength of 880 nm is included in the transmission band and 660 nm is not included in the transmission band, a long pass filter that transmits only light having a wavelength equal to or greater than a wavelength longer than the wavelength of 660 nm and shorter than the wavelength of 880 nm, or the like can be considered. In this explanation, it is needless to say that "transmit" or "does not transmit" includes a case of "transmit" or "does not transmit" most of light.

In the present embodiment, the light intensity detector 14 disposed in the probe 10*a* includes a plurality of light intensity detectors that selectively detect reflected light of a plurality of correction light beams having different wavelengths. For example, the first light intensity detector 14*a* does not detect the reflected light of the second correction light, and the second light intensity detector 14*b* does not detect the reflected light of the first correction light. In the case of using the probe 10*a* having such a configuration, it is possible to simultaneously emit a plurality of correction light beams from the correction light source 13. For example, it is possible to simultaneously emit the first correction light and the second correction light and to simultaneously detect the reflected light beams. In this manner, there is an effect that the time required to estimate the amount of melanin can be shortened. Other effects are the same as in the first embodiment.

Figure 6:
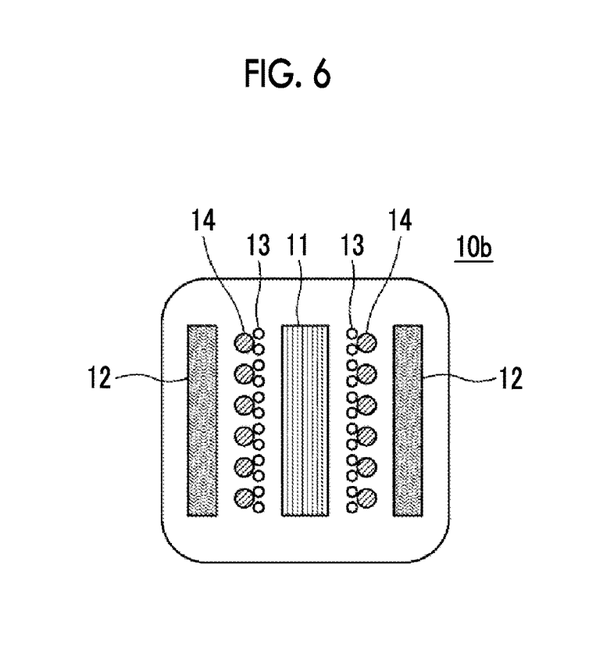
FIG. 6 is a plan view showing a probe according to a third embodiment of the present invention.

Subsequently, a third embodiment of the present invention will be described. FIG. 6 shows a probe according to the third embodiment of the present invention. The present embodiment is different from the first embodiment in that the light intensity detector 14 disposed in a probe 10*b* detects the reflected light of measurement light emitted from the measurement light emitting unit 12 in addition to detecting the reflected light of correction light emitted from the correction light source 13. In the present embodiment, the wavelength of measurement light emitted from the light source 30 (FIG. 1) is different from the wavelength of the correction light emitted from the correction light source 13. Others may be the same as in the first embodiment.

Figure 7:
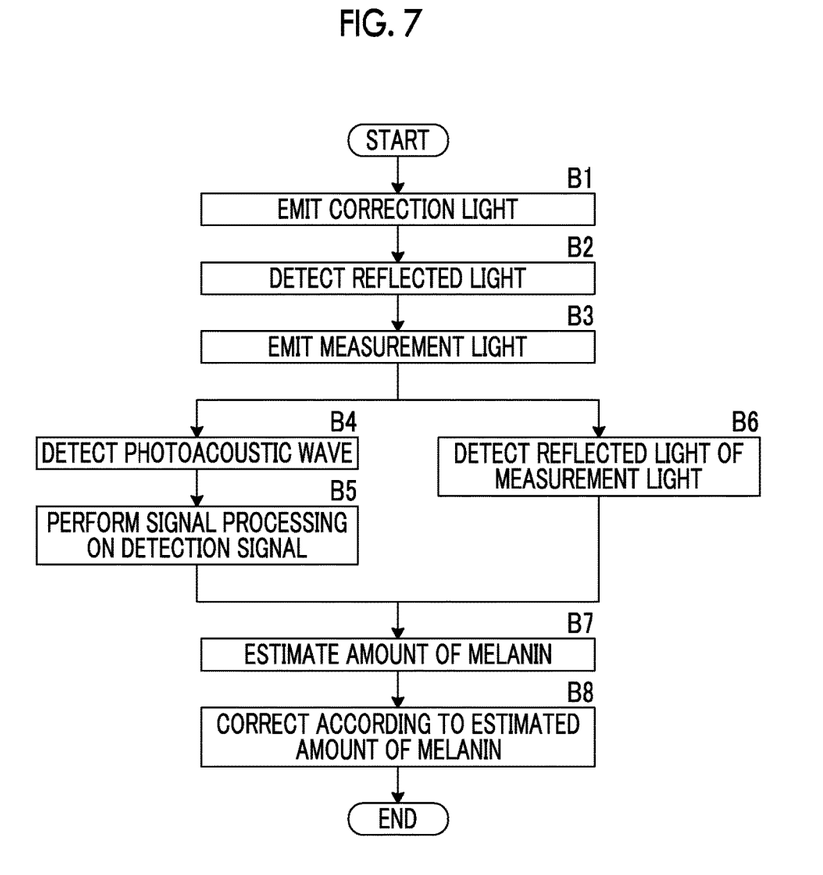
FIG. 7 is a flowchart showing the operation procedure of photoacoustic measurement in the third embodiment.

FIG. 7 shows the operation procedure of photoacoustic measurement in the present embodiment. A doctor or the like presses the probe 10*b* against an examination part of the subject. The light source control unit 26 (refer to FIG. 3) turns on the correction light source 13 to emit correction light to the subject (step B1). The light intensity detector 14 detects the reflected light of the correction light, and transmits the detection signal to the signal processing device 20 (step B2).

Then, the light source control unit 26 causes the light source 30 (refer to FIG. 1) to emit measurement light (step B3). The acoustic wave detector 11 detects photoacoustic waves generated within the subject due to the emission of the measurement light (step B4). The detection signal of the photoacoustic wave is input to the signal processing unit 23 through the receiving circuit 21 and the receiving memory 22. The signal processing unit 23 performs signal processing on the detection signal of the photoacoustic wave (step B5). The signal processing unit 23 generates a photoacoustic image, for example.

On the other hand, the light intensity detector 14 detects the reflected light of the measurement light emitted in step B3, and transmits the detection signal to the signal processing device 20 (step B6). The melanin amount estimation unit 24 estimates the amount of melanin of a portion, against which the probe 10*b* is pressed, based on the detection signal of the reflected light of the correction light and the detection signal of the reflected light of the measurement light that have been received from the light intensity detector 14 (step B7). In a case where there is a large level difference between the detection signal of the reflected light of the correction light and the detection signal of the reflected light of the measurement light, the melanin amount estimation unit 24 may estimate the amount of melanin after correcting the level difference.

The correction unit 25 corrects the signal processing of the signal processing unit 23, for example, image generation, according to the amount of melanin estimated in step B7 (step B8). The correction may be the same as that described in the first embodiment.

In the present embodiment, the light intensity detector 14 detects the reflected light of the measurement light emitted from the measurement light emitting unit 12 in addition to the reflected light of the correction light emitted from the correction light source 13. In the present embodiment, one wavelength among a plurality of wavelengths used in estimating the amount of melanin is obtained from the measurement light for photoacoustic measurement. In such a case, the correction light source 13 does not need to emit correction light beams having a plurality of wavelengths. Therefore, it is possible to reduce the number of types (wavelengths) of correction light source that need to be disposed in the probe 10*b*. In addition, in a case where the detection of photoacoustic waves and the detection of reflected light are performed in parallel, there is an effect that the time required to estimate the amount of melanin can be shortened. Other effects are the same as in the first embodiment.

Although the emission of measurement light and the detection of photoacoustic waves are performed after estimating the amount of melanin in FIG. 4, the timing of the emission of measurement light and the detection of photoacoustic waves are not particularly limited. The emission of measurement light and the detection of photoacoustic waves may be performed before the emission of the first correction light, or the emission of measurement light and the detection of photoacoustic waves may be performed between the emission of the first correction light and the emission of the second correction light. The signal processing on the detection signal of the photoacoustic wave (step A8) and the correction according to the estimated amount of melanin (step A9) do not need to be separated, and the signal processing in step A8 may be performed according to the correction content in step A9.

In addition, although the emission of measurement light, detection of photoacoustic waves, and detection of reflected light are performed after the emission of correction light and detection of reflected light in FIG. 7, the order is not particularly limited. The measurement light may be emitted first and the detection of photoacoustic waves and the detection of the reflected light of the measurement light may be performed, and then correction light may be emitted and the reflected light may be detected. In the same manner as described above, the signal processing on the detection signal of the photoacoustic wave (step B5) and the correction according to the estimated amount of melanin (step B8) do not need to be separated, and the signal processing in step B5 may be performed according to the correction content in step B8.

In FIG. 7, the detection of photoacoustic waves (step B4) and the detection of reflected light (step B6) are performed in parallel after emitting the measurement light in step B3, the present invention is not necessarily limited thereto. Either the detection of photoacoustic waves or the detection of reflected light may be performed every emission of measurement light. Usually, the repetition frequency of the light source 30 used for photoacoustic measurement is about 10 Hz to 30 Hz. Accordingly, from the viewpoint of shortening the repetition period of photoacoustic measurement, it is advantageous to output no separate measurement light for detecting the reflected light.

The relationship between the estimation of the amount of melanin and the detection of photoacoustic waves may not be a one-to-one relationship. For example, means capable of detecting the movement of the probe 10 may be provided, and the amount of melanin may be estimated by performing the emission of correction light and the detection of reflected light in a case where the movement of the probe 10 is detected. In a case where there is no movement of the probe 10, correction according to the amount of melanin estimated at that position may be applied to signal processing on the detection signal of the photoacoustic wave that is performed multiple times.

Although the amount of melanin is estimated mainly based on the reflected light beams having two wavelengths, the amount of melanin may be corrected based on the reflected light beams having three or more wavelengths. For example, the correction light source 13 may include light sources that emit correction light beams having three or more wavelengths, the light intensity detector 14 may detect reflected light beams of the correction light beams having three or more wavelengths, and the melanin amount estimation unit 24 may estimate the amount of melanin based on the detection signal of the reflected light beams of the correction light beams having three or more wavelengths. By increasing the number of wavelengths of reflected light used for estimation, it is possible to improve the accuracy of melanin amount estimation.

The respective embodiments described above can be appropriately used in combination. For example, the first and third embodiments may be combined, so that the light intensity detector 14 detects the reflected light of the first correction light, the reflected light of the second correction light, and the reflected light of the measurement light and the melanin amount estimation unit 24 estimates the amount of melanin based on the detection signal of the reflected light. In addition, the second and third embodiments may be combined, so that the light intensity detector 14 is configured to include a light intensity detector that selectively detects the reflected light of the first correction light, a light intensity detector that selectively detects the reflected light of the second correction light, and a light intensity detector that selectively detects the reflected light of the measurement light.

While the present invention has been described based on the preferred embodiments, the photoacoustic measurement apparatus and the probe of the present invention are not limited to the above embodiments, and various modifications and changes in the configurations of the above embodiments are also included in the range of the present invention.

EXPLANATION OF REFERENCES

10: probe
11: acoustic wave detector
12: measurement light emitting unit
13: correction light source
14: light intensity detector
20: signal processing device
21: receiving circuit
22: receiving memory
23: signal processing unit
24: melanin amount estimation unit
25: correction unit
26: light source control unit
30: light source
40: image display device

What is claimed is:

1. A photoacoustic measurement apparatus, comprising:
a probe; and
a processor,
wherein the probe comprising:
a measurement light emitting unit that emits measurement light toward a subject;
an acoustic wave detector that detects a photoacoustic wave generated within the subject due to the measurement light;
a correction light source that emits correction light toward the subject;
a light intensity detector that detects reflected light generated by reflection of the correction light, which is emitted toward the subject, from the subject, and
wherein the correction light source and the light intensity detector are disposed between the measurement light emitting unit and the acoustic wave detector,
wherein the correction light source includes a first correction light source, which is arranged along the one direction and emits first correction light having a first wavelength, and a second correction light source, which is arranged along the one direction and emits second correction light having a second wavelength different from the first wavelength, and
wherein the acoustic wave detector includes a plurality of detector elements arranged along one direction,
and
wherein the processor configured to estimate an amount of melanin based on a detection signal of reflected light of the first correction light detected by the light intensity detector and a detection signal of reflected light of the second correction light detected by the light intensity detector.

2. The photoacoustic measurement apparatus according to claim 1,
wherein the measurement light emitting unit includes a light emission surface, which is a surface from which the measurement light is emitted, and the acoustic wave detector includes an acoustic wave detection surface, which is a surface on which the acoustic wave is incident, and
the correction light source and the light intensity detector are disposed within the same plane as the light emission surface and the acoustic wave detection surface.

3. The photoacoustic measurement apparatus according to claim 1,
wherein a plurality of the measurement light emitting units are provided, and the plurality of measurement light emitting units face each other with the acoustic wave detector interposed therebetween in a direction perpendicular to the one direction, and
the correction light source and the light intensity detector are disposed between the measurement light emitting unit and the acoustic wave detector.

4. The photoacoustic measurement apparatus according to claim 2,
wherein a plurality of the measurement light emitting units are provided, and the plurality of measurement light emitting units face each other with the acoustic wave detector interposed therebetween in a direction perpendicular to the one direction, and the correction light source and the light intensity detector are disposed between the measurement light emitting unit and the acoustic wave detector.

5. The photoacoustic measurement apparatus according to claim 1,
wherein the correction light source includes a plurality of the first correction light sources and a plurality of the second correction light sources.

6. The photoacoustic measurement apparatus according to claim 5,
wherein the plurality of first correction light sources and the plurality of second correction light sources are alternately arranged along the one direction.

7. The photoacoustic measurement apparatus according to claim 1,
wherein the light intensity detector includes a first light intensity detector, which is arranged along the one direction and selectively detects correction light having the first wavelength, and a second light intensity detector, which is arranged along the one direction and selectively detects correction light having the second wavelength.

8. The photoacoustic measurement apparatus according to claim 7,
wherein the first light intensity detector includes a first optical filter that transmits light having the first wavelength and does not transmit light having the second wavelength, and
the second light intensity detector includes a second optical filter that transmits light having the second wavelength and does not transmit light having the first wavelength.

9. The photoacoustic measurement apparatus according to claim 7,
wherein the light intensity detector includes a plurality of the first light intensity detectors and a plurality of the second light intensity detectors.

10. The photoacoustic measurement apparatus according to claim 9,
wherein the plurality of first light intensity detectors and the plurality of second light intensity detectors are alternately arranged along the one direction.

11. The photoacoustic measurement apparatus according to claim 1,
wherein a wavelength of the measurement light and a wavelength of the correction light are different from each other, and
the light intensity detector further detects reflected light generated by reflection of the measurement light, which is emitted toward the subject, from the subject.

12. The photoacoustic measurement apparatus according to claim 1,
wherein the correction light source includes a light emitting diode.

13. The photoacoustic measurement apparatus according to claim 1, comprising:
a light source that emits the measurement light,
wherein the processor further configured to perform signal processing based on a detection signal of the photoacoustic wave detected by the acoustic wave detector, and correct the signal processing.

14. The photoacoustic measurement apparatus according to claim 13,
wherein the processor further configured to generate a photoacoustic image based on the detection signal of the photoacoustic wave.

15. A photoacoustic measurement apparatus, comprising:
a probe; and
a processor
wherein the probe comprising:
a measurement light emitting unit that emits measurement light toward a subject;
an acoustic wave detector that detects a photoacoustic wave generated within the subject due to the measurement light;
a correction light source that emits correction light toward the subject;
a light intensity detector that detects reflected light generated by reflection of the correction light, which is emitted toward the subject, from the subject, and
wherein the correction light source and the light intensity detector are disposed between the measurement light emitting unit and the acoustic wave detector,
wherein a wavelength of the measurement light and a wavelength of the correction light are different from each other, and
the light intensity detector further detects reflected light generated by reflection of the measurement light, which is emitted toward the subject, from the subject,
and
wherein the processor configured to estimate an amount of melanin based on a detection signal of reflected light of the correction light detected by the light intensity detector and a detection signal of reflected light of the measurement light detected by the light intensity detector.

16. The photoacoustic measurement apparatus according to claim 15,
wherein the measurement light emitting unit includes a light emission surface, which is a surface from which the measurement light is emitted, and the acoustic wave detector includes an acoustic wave detection surface, which is a surface on which the acoustic wave is incident, and
the correction light source and the light intensity detector are disposed within the same plane as the light emission surface and the acoustic wave detection surface.

17. The photoacoustic measurement apparatus according to claim 15,
wherein the acoustic wave detector includes a plurality of detector elements arranged along one direction.

18. The photoacoustic measurement apparatus according to claim 17,
wherein a plurality of the measurement light emitting units are provided, and the plurality of measurement light emitting units face each other with the acoustic wave detector interposed therebetween in a direction perpendicular to the one direction, and
the correction light source and the light intensity detector are disposed between the measurement light emitting unit and the acoustic wave detector.

19. The photoacoustic measurement apparatus according to claim 17,
wherein the correction light source includes a first correction light source, which is arranged along the one direction and emits first correction light having a first wavelength, and a second correction light source, which is arranged along the one direction and emits second correction light having a second wavelength different from the first wavelength.

20. The photoacoustic measurement apparatus according to claim 19, wherein the correction light source includes a plurality of the first correction light sources and a plurality of the second correction light sources.

21. The photoacoustic measurement apparatus according to claim 20,
wherein the plurality of first correction light sources and the plurality of second correction light sources are alternately arranged along the one direction.

22. The photoacoustic measurement apparatus according to claim 17,
wherein the light intensity detector includes a first light intensity detector, which is arranged along the one direction and selectively detects correction light having the first wavelength, and a second light intensity detector, which is arranged along the one direction and selectively detects correction light having the second wavelength.

23. The photoacoustic measurement apparatus according to claim 22,
wherein the first light intensity detector includes a first optical filter that transmits light having the first wavelength and does not transmit light having the second wavelength, and
the second light intensity detector includes a second optical filter that transmits light having the second wavelength and does not transmit light having the first wavelength.

24. The photoacoustic measurement apparatus according to claim 22,
wherein the light intensity detector includes a plurality of the first light intensity detectors and a plurality of the second light intensity detectors.

25. The photoacoustic measurement apparatus according to claim 24,
wherein the plurality of first light intensity detectors and the plurality of second light intensity detectors are alternately arranged along the one direction.

26. The photoacoustic measurement apparatus according to claim 15,
wherein the correction light source includes a light emitting diode.

27. The photoacoustic measurement apparatus according to claim 15, comprising:
a light source that emits the measurement light,
wherein the processor further configured to perform signal processing based on a detection signal of the photoacoustic wave detected by the acoustic wave detector, and correct the signal processing.

28. The photoacoustic measurement apparatus according to claim 27,
wherein the processor further configured to generate a photoacoustic image based on the detection signal of the photoacoustic wave.

* * * * *